United States Patent [19]

Doerr et al.

[11] 4,408,605

[45] Oct. 11, 1983

[54] DEVICE FOR TREATMENT OF BAROTRAUMA OF THE MIDDLE EAR

[76] Inventors: John D. Doerr, 2601 E. Camino Principal; Donn G. Duncan, 6135 E. Miramar Dr., both of Tucson, Ariz. 85715

[21] Appl. No.: 318,831

[22] Filed: Nov. 6, 1981

[51] Int. Cl.³ .............................................. A61F 7/00
[52] U.S. Cl. .................................. 128/402; 128/403; 128/151
[58] Field of Search .............................. 128/399–403, 128/151–152, 132 R

[56] References Cited

U.S. PATENT DOCUMENTS

| 3,643,665 | 2/1972 | Caillouette | 128/403 |
| 3,796,855 | 3/1974 | Brown et al. | 128/399 X |
| 3,938,614 | 2/1976 | Ahs | 128/151 X |
| 4,023,642 | 5/1977 | Korn | 128/152 X |
| 4,308,623 | 1/1982 | Voorhees | 128/151 X |

FOREIGN PATENT DOCUMENTS 1078579  11/1954  France .............................. 128/151
598030   2/1948   United Kingdom .............. 128/152

Primary Examiner—Lee S. Cohen
Assistant Examiner—Angela D. Sykes
Attorney, Agent, or Firm—William H. Drummond

[57] ABSTRACT

A device for treatment of barotrauma of the middle ear includes a flexible backing portion carrying a peripheral annular cushion portion which fits over and encloses the outer ear. The cushion portion is deformable under hand pressure applied against the flexible backing to fit the contours of the exterior portion of the head around the outer ear. A hand pressure-activated chemical heating package is carried in the device. The package contains chemicals separated in separate compartments. When one of the compartments is ruptured and the chemicals subsequently mixed, an exothermic reaction is produced.

The heat generated by the exothermic reaction, when the device is held over the outer ear, is transmitted to the inner ear to treat the barotrauma by directly reducing its painful effects and by increasing the volume of the air in the middle ear.

1 Claim, 6 Drawing Figures

U.S. Patent    Oct. 11, 1983    4,408,605
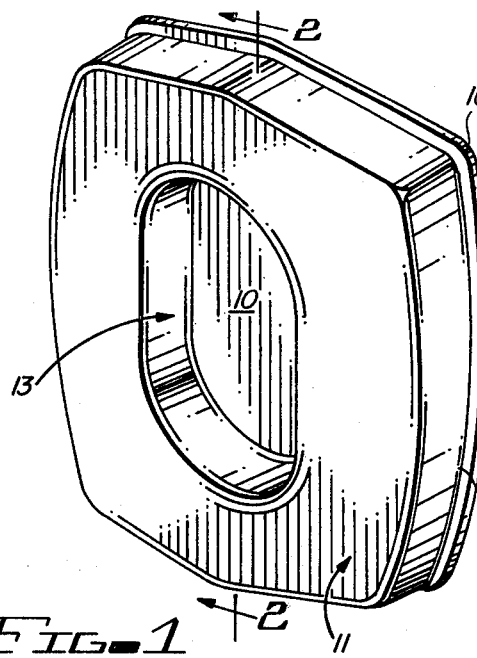
FIG. 1
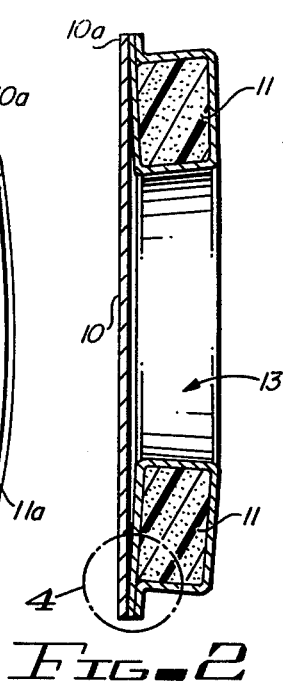
FIG. 2
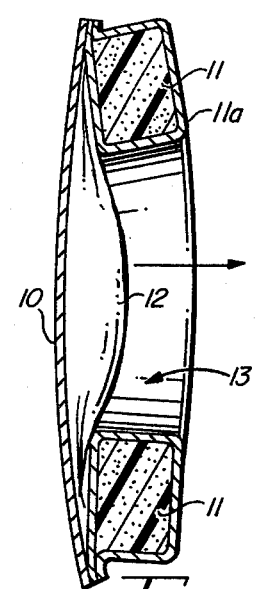
FIG. 3
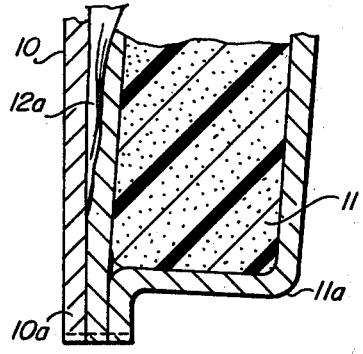
FIG. 4
FIG. 6
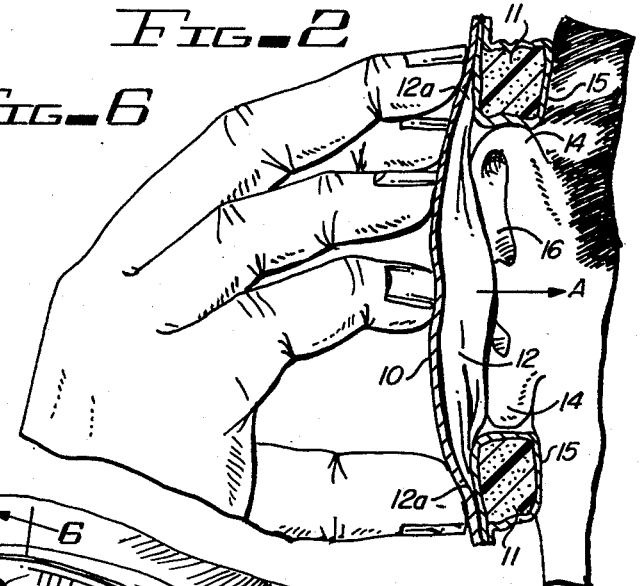
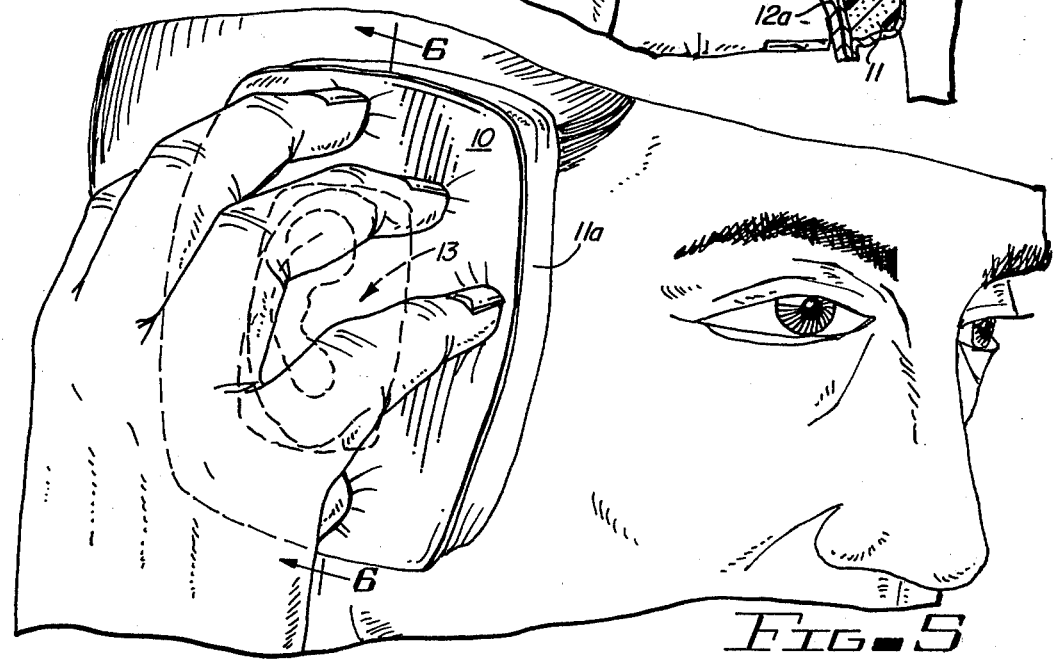
FIG. 5

DEVICE FOR TREATMENT OF BAROTRAUMA OF THE MIDDLE EAR

This invention pertains to a device for treatment of barotrauma of the middle ear.

In another respect, the invention concerns a device which can be easily activated and used by persons having little or no medical skills to treat barotrauma.

In still another aspect, the invention pertains to a very inexpensive device which, after use, can either be conveniently discarded or re-used after appropriate sterilization and replacement of one of the disposable components thereof.

In yet another respect, the invention concerns a device for treatment of barotrauma which is wholly self-contained and which requires no external components for its activation and operation.

For the purposes of explaining the present invention, the ear may be conveniently considered as consisting of three main sub-components—the outer ear, including the auditory canal, the middle ear separated by a membranous "eardrum" from the outer ear, and the inner ear which is separated from the middle ear by membranous fenestrae.

The middle ear, or tympanum, is an irregular cavity, compressed from without inwardly and situated within the petrous bone. It is filled with air and communicates with the naso-Pharynx by the Eustachian tube. The middle ear is traversed by a chain of movable bones which serve to transmit vibrations of the eardrum across the middle ear to the fenestrae which separates the middle ear from the inner ear.

Thus, it will be observed that except for the Eustachian tube which connects the middle ear to the nasopharynx, the middle ear would be a closed cavity. Under certain conditions, the Eustachian tube can be blocked by swelling caused by irritation, e.g., under the conditions of the common head cold. When such blockage occurs and the ambient pressure increases with respect to the pressure within the middle ear, e.g., upon descent in an airplane, the increased ambient pressure tends to deform the eardrum inwardly and this deformation can cause severe pain called "barotrauma."

It is known that application of heat to the tympanic membrane and middle ear can partially or completely alleviate the pain of barotrauma. For example, it is common practice on some commercial airlines for the stewardess to furnish a passenger suffering from barotrauma with a hot washcloth stuffed into a coffe cup, which the passenger can then place against his ear. The heat transmitted to the middle ear has two therapeutic effects—first, the normal analgesic effect of the application of heat to any painful body member and, secondly, the heat causes an expansion of the air trapped within the middle ear which causes the eardrum to return to its normal position instead of being deformed inwardly.

The procedure described above, involving the use of a hot washcloth and coffee cup, is at least undesirable because it is "messy" but, more importantly, there is no accurate way of controlling the amount of heat transferred to the inner ear and this procedure may even pose a threat of inducing infection due to non-sterility of the cup, washcloth, or water used to wet the washcloth.

The closest prior art of which we are aware is U.S. Pat. No. 3,796,855, issued to Brown et al., on Mar. 12, 1974, which discloses a portable device which can be carried on a person in order to relieve "earache pain" caused by thermal effects such that it can be worn outside on windy or cold days when such weather conditions further aggravate the earache. The Brown et al device contains an electrical heating element which can be operated either on household electric current or the current from a dry-cell battery. The electrical heating element is enclosed within a solid housing and appears to be fitted with a resilient annular pad such that the device can be placed comfortably against, but not around, the pinna portion of the auricle (see, e.g., Brown et al FIG. 2). As so disclosed, the Brown et al device does not appear to provide or rely upon anything other than the analgesic effect of applying heat and/or protecting the wearer's ear from undesirable thermal effects. Also, of considerable interest in connection with our present invention, U.S. Pat. No. 3,804,077 to Williams, entitled "Hot or Cold Pack," issued Apr. 16, 1974, discloses a package divided into two compartments containing chemicals which, upon rupture of one of the compartments and mixture of the chemicals, produce either exothermic or endothermic chemical reactions. The entire pack can be placed against a person or an object to transfer heat from or to the person or object. And see U.S. Pat. No. 4,057,047 to Gossett, entitled "Magnesium Sulfate Anhydrous Hot Pack, etc.," issued Nov. 8, 1977.

Other prior art which discloses the application of heat to body members which is generated by exothermic chemical reactions include U.S. Pat. No. 3,320,682 to Sliman, entitled "Curler Bonnet," issued May 23, 1967, which promotes and accelerates the drying of wet hair; U.S. Pat. No. 3,542,032 to Spencer, entitled "Therapy Package," issued Nov. 24, 1970; U.S. Pat. No. 3,774,589 to Kober, entitled "Self-contained Electrochemical Heating Source," issued Nov. 27, 1973; U.S. Pat. No. 3,893,834 to Armstrong, entitled "Insulated Cold Pack," issued July 8, 1975; U.S. Pat. No. 3,149,943 to Amador, entitled "Chemical Refrigerant Package," issued Sept. 22, 1964; and U.S. Pat. No. 3,865,117 to Perry, entitled "Thermal Compress, etc." issued Feb. 11, 1975.

In view of the obvious disadvantages of the practices now employed by commercial airlines and the failure of the prior art to provide an effective, simple and inexpensive device for treating barotrauma of the middle ear, it would be highly advantageous to provide a device of simplified construction, which would be useful by persons with little or no medical skills, which could be economically constructed to the point of being disposable or at least partially disposable.

Accordingly, it is the principal object of the present invention to provide a device for treating barotrauma of the middle ear.

Another object of the present invention is to provide such a device which is of simplified construction and use by non-medically trained persons or the user, himself.

Yet another object of the invention is to provide such a device which can be simply and economically constructed.

Still another object of the invention is to provide such a device which is partially and/or totally disposable and which can be sterilized and easily maintained in sterilized condition until just prior to use.

These and other, further and more specific objects and advantages of the present invention will be apparent to those skilled in the art from the following detailed description thereof, taken in conjunction with the drawings, in which:

FIG. 1 is a perspective view of the backing portion and annular cushion portion of the presently preferred embodiment of the invention, chosen for purposes of illustration and not by way of limitation;

FIG. 2 is a sectional view of the outer covering including backing portion and annular cushion portion, taken along section line 2—2 of FIG. 1;

FIG. 3 is a sectional view of the device of FIG. 1 taken along section line 2—2 thereof but including the chemical heating package assembled therewith;

FIG. 4 is an expanded sectional view of the circled portion 4 of FIG. 2;

FIG. 5 is a perspective view showing the device of FIGS. 1-4 in operative position against the user's head and around the user's ear; and FIG. 6 is a sectional view of FIG. 5 taken along section line 6—6 thereof.

Briefly, in accordance with our invention, we provide a device for treatment of barotrauma of the middle ear. The device consists of a flexible backing portion, an annular cushion portion carried by the backing which is shaped and adapted to fit over and enclose the pinna of the outer ear and which is deformable under hand pressure against the backing to fit the exterior portion of the head around the auricle, and a hand pressure-activated chemical heating package retained in the device. The chemical heating package contains chemicals which are separated in separate compartments and which, upon rupture of one of the compartments and mixing of the chemicals, produce an exothermic reaction. The heat generated by the exothermic reaction is transmitted, when the device is held in operative position, to the middle ear to treat the barotrauma by combination of the direct analgesic effect which reduces the painful effects of the barotrauma and by increasing the volume of the air contained within the middle ear to reduce the deformation of the eardrum caused by a differential negative pressure within the middle ear.

Turning now to the drawings, in which like reference numerals demote the same elements in the several views, the presently preferred embodiment of the invention includes a flexible backing portion 10, e.g., fabricated of PVC or similar material, an annular cushion portion 11 carried by the backing 10 and a hand pressure-activated chemical heating package 12 retained within the device. The annular cushion portion 11 may be suitably fabricated, for example, for polyurethane foam and, as shown, is enclosed by a covering portion 11A which is affixed to the backing member 10 around the periphery 10A thereof by any suitable means, such as heat sealing, glueing, etc. The peripheral portions 12A are received in the space between the backing member 10 and the covering portion 11A of the cushion 11 to retain the chemical heating package within the device. If desired, after use, the chemical heating package 12 may be removed from the device and replaced with a fresh package after sterilization of the backing 10 and cushion member 11 so as to make the device, except for the replacement heating package, re-usable.

As will appear from the drawings, especially FIG. 6, the opening 13 defined by the annular member 11 is shaped and adapted to fit over and enclose the pinna 14 of the outer ear and is deformable under hand pressure (as shown in FIG. 6) to fit the contours of the exterior portion 15 of the head and neck around the auricle 16.

In this operative position, the device may be comfortably held around the auricle with the annular cushion 11 semi-sealingly engaging the exterior portion 15 of the head and neck of the user so as to prevent heat loss while affording maximum comfort to the user.

The hand pressure-activated chemical heating package may be any one of several of such known devices which contain chemicals separated therewithin in separate compartments and which, upon rupture of one of the compartments and subsequent mixing of the chemicals, produce an exothermic reaction. For example, a suitable chemical heating package which may be used in accordance with the presently preferred embodiment of the invention is disclosed in U.S. Pat. No. 3,804,077 issued to Vernon L. Williams, entitled "Hot or Cold Pack" on Apr. 16, 1974. Such devices are commercially available.

In operation, simple thumb pressure on the unactivated chemical heating package 12 and the underlying portion of the flexible backing member 10 causes the rupture of one of the internal compartments and the chemicals and other materials within the package 12 can then be thoroughly and conveniently mixed by simply hand-kneading the entire device by crushing it in the palm of the user or attendant. After the chemicals are mixed and the exothermic reaction begins, the device is placed in its proper operative position as shown in FIGS. 5-6 and heat is transferred in the direction of the arrow A through the auditory canal to the middle ear of the user. Heat serves to directly reduce the painful effects of the barotrauma by the well-known analgesic effect of heat on any portion of the human body and by producing a small but effective increase in the volume of air within the middle ear by heating the air, causing it to expand. Expansion of the volume of air trapped within the middle ear because of a blocked or partially blocked Eustachian tube serves to deflect the eardrum which separates the middle ear from the outer ear outwardly toward its normal position, thereby effectively reducing the pain which accompanies the deflection of the eardrum inwardly, which is the chief reason for the pain associated with barotrauma. As will be observed, the entire device, including the chemical heting package, can be conveniently sterilized and placed in sealed, openable containers until just prior to use, thus assuring that use and re-use of the device will not induce infection in the ear of the user.

Having described our invention in such terms as to enable those skilled in the art to practice it, and having identified the presently preferred embodiments thereof,

We claim:

1. A device for treatment of barotrauma of the middle ear, said device comprising, in combination:
   (a) a flexible backing portion, crushable by hand-kneading;
   (b) an annular cushion portion carried by said backing portion, shaped and adapted to fit over and enclose the pinna of the outer ear and being deformable under hand pressure against said backing portion to fit the contours of the exterior portion of the head and neck around the auricle; and
   (c) a hand pressure-activated chemical heating package retained by the backing and annular cushion portions and exposed to the opening of the cushion portion, said package containing chemicals separated therewithin in separate compartments and which, upon rupture of one of the compartments and subsequent mixing of said chemicals by crushing and hand-kneading, produces an exothermic reaction, such that when said device is held in operative position over and enclosing the pinna and against the exterior portion of the head and neck around the auricle, the heat generated by said exothermic reaction is transmitted to the middle ear to treat said barotrauma by directly reducing the painful effects thereof and by increasing the volume of the air contained therewithin.

* * * * *